United States Patent [19]
Allard et al.

[11] Patent Number: 6,050,974
[45] Date of Patent: Apr. 18, 2000

[54] RETRACTABLE HYPODERMIC NEEDLE

[76] Inventors: Edward F. Allard, 7830 Greeley Blvd., Springfield, Va. 22152; Daniel Q. Longmire, 14625 Balimore Ave., Laurel, Md. 20707

[21] Appl. No.: 09/352,145

[22] Filed: Jul. 13, 1999

[51] Int. Cl.[7] .................................................. A61M 5/00
[52] U.S. Cl. ........................................... 604/110; 604/195
[58] Field of Search ..................................... 604/110, 192, 604/195, 263, 187, 218

[56] References Cited

U.S. PATENT DOCUMENTS

| | | | |
|---|---|---|---|
| 5,015,234 | 5/1991 | Jullien | 604/110 |
| 5,295,973 | 3/1994 | Chen | 604/110 X |
| 5,342,310 | 8/1994 | Veyama et al. | 604/195 X |

*Primary Examiner*—John D. Yasko

[57] ABSTRACT

An automatically retractable hypodermic needle incorporating a spring loaded needle assembly held in place by a rotatable member having a dislodgable filler sleeve extending through a hole in the rotatable member, such that upon the application of downward pressure by the plunger on the edge of the rotatable member, the member is rotated and the dislodgable filler sleeve is aligned with the spring loaded needle assembly, allowing the needle assembly to force the filler sleeve out of the hole in the rotatable member, and accordingly, allow the filler sleeve and needle assembly to be automatically retracted into the barrel of the plunger.

10 Claims, 4 Drawing Sheets

RETRACTABLE HYPODERMIC NEEDLE

BACKGROUND OF THE INVENTION

1. Field of the Invention

The present invention generally relates to devices and techniques for protecting one from the accidental pricking of oneself with the expended needle of a hypodermic syringe resulting in exposure to blood carrying viruses and diseases, such as AIDS and the hepatitis viruses, and more specifically, to a hypodermic syringe, having incorporated therein an automatically retracting needle, which is safely housed within the body of the syringe after retraction, and to a method and apparatus for controlling the speed of retraction of an automatically retracting needle, as well as a method and syringe design for capturing any body fluids adhering to the surface of the needle upon retraction of the needle from a patient. Contaminated needles carry a host of infectious agents on the surface of the needle, as well as in the hollow-bore of the needle. Accidental needle sticks to health-care workers, prison personnel and emergency workers, such as paramedics and firefighters occur to more than a million health-care workers every year, and for many it is a death sentence.

2. Description of Prior Art

A number of techniques have been employed in the medical field to help reduce the inadvertent exposure to hypodermically derived body fluids from a patient, to include a range of efforts extending from that of manually providing a sheath to cover the needle after use, breaking the needle from the syringe housing and disposing of it, to that of retracting the needle assembly of the hypodermic syringe into the body of the syringe, but in each instance, except that of U.S. Pat. No. 4,838,869, having the same inventorship as the instant application, there has been no truly automatically retractable needle that could be effectively manufactured and employed to meet the needs of the industry.

SUMMARY OF THE INVENTION

The primary purpose of this invention is to help alleviate the problem in the medical field of secondary infections derived from the inadvertent exposure of a health-care worker to the body fluids of a patient, resulting from the use of hypodermic needles on the patient. A secondary purpose is to render a spent needle unusable, to avoid the inadvertent transmission of viruses and diseases to a secondary user. The instant invention overcomes all the presently known problems related to the inadvertent transfer of contagious viruses and diseases to a healthcare worker, resulting from the use of a hypodermic needle on a patient. In essence, the instant solution to the above noted problems comprises a somewhat radically new design for a hypodermic syringe, which includes, as in most syringes, a syringe housing for accommodating a syringe plunger, but from this point on there is little resemblance to the typical hypodermic syringe. The present invention uses a spring loaded needle assembly held in place by a rotatable member having a dislodgable filler sleeve extending through the rotatable member, such that upon the application of downward pressure by the plunger on the edge of the rotatable member, the member is rotated and the dislodgable filler sleeve is aligned with the spring loaded needle assembly, allowing the spring loaded needle assembly to force the filler sleeve out of the rotatable member, whereby the filler sleeve and needle assembly is automatically retracted into the barrel of the plunger. The reference to "retracted" in this instance, is intended to define the act of actually retracting a needle from the body of a patient and forcing, not necessarily retracting, the needle and needle assembly of the hypodermic syringe into a storage area within the plunger of the syringe. The fluid ejection end of the syringe housing further includes a syringe housing extension for housing the needle assembly and contains a seal, through which the needle extends, which not only serves as a seal against the seepage of fluids from the syringe, but also functions to provide just the predetermined amount of compression and friction on the needle to control the speed of retraction of the needle. The syringe housing extension is further designed to accommodate a fluid catch basin within the extreme tip thereof to collect any body fluids that may have adhered to the needle or be infecting the bore of the needle upon extraction from the body of the patient. Upon retraction of the needle through the syringe seal, the needle is wiped clean by the friction of the seal on the surface of the needle, such that any body fluids swept from the needle is caught in the catch basin in the tip of the syringe housing extension.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
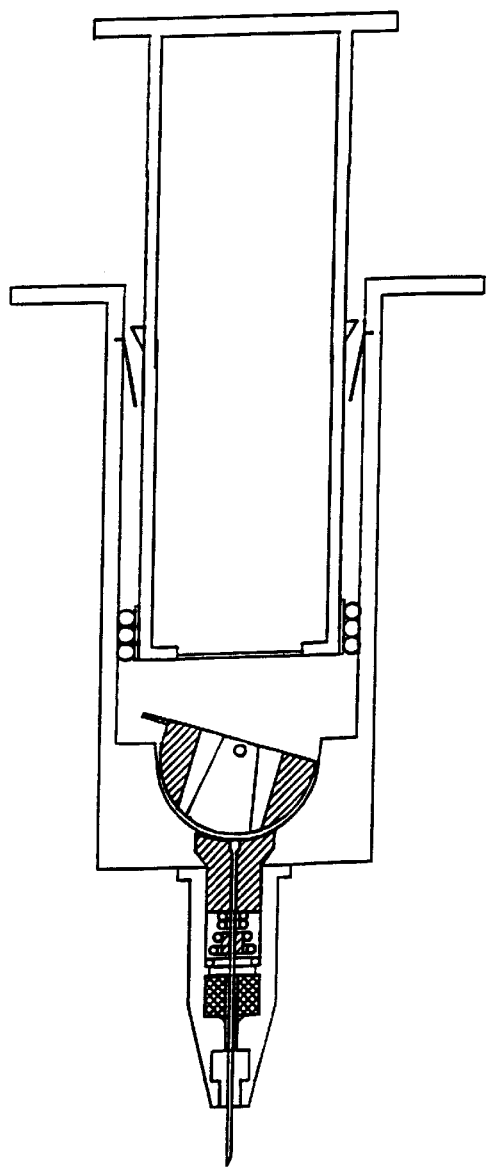
FIG. 1 is a cutaway view of the instant invention in a static position.
Figure 2:
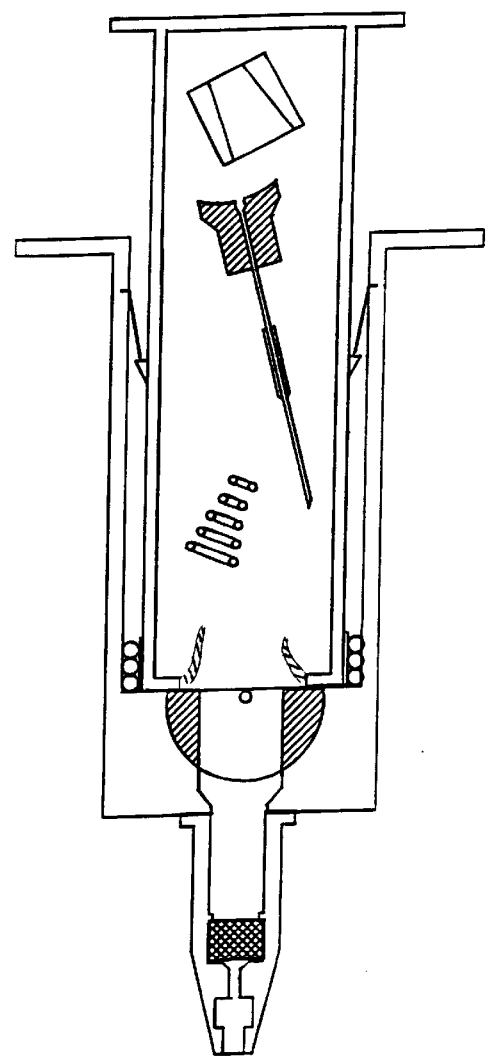
FIG. 2 is a cutaway view of the instant invention after the needle has been retracted into the barrel of the plunger.

Referring now to the drawings, and more particularly to FIGS. 1 and 2, we respectively see a depiction of the state of the needle before the syringe is filled with an injectable fluid, as well as the state of the various elements after retraction of the needle assembly into the barrel of the syringe plunger.

Figure 3:
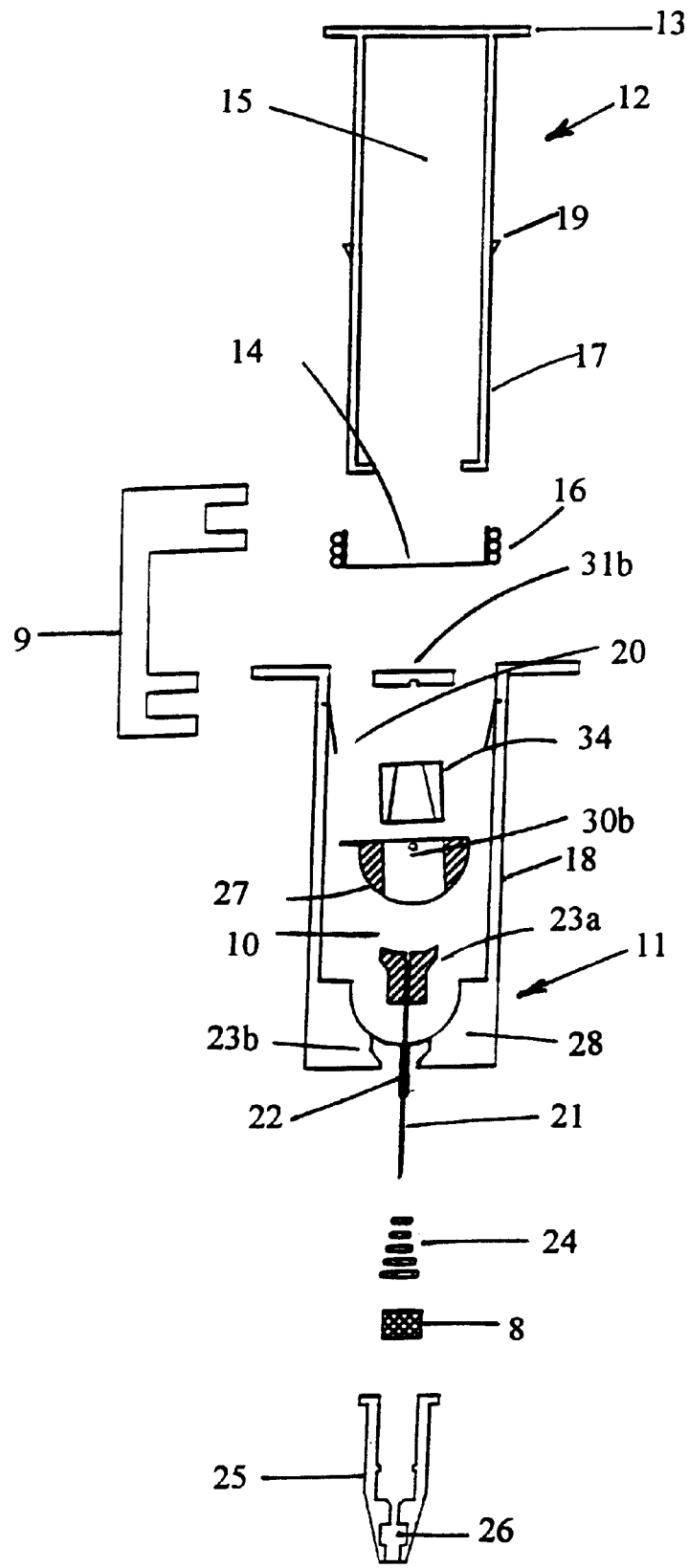
FIG. 3 is a cutaway-exploded view of the instant invention.

A description of the various components within the automatically retractable hypodermic syringe will best be understood my referring to FIG. 3, where all the elements of the hypodermic syringe are shown in cross-section, and exploded, in order to better show the functional relationship between the various elements. FIG. 3 shows one of the preferred embodiments of the invention, wherein a syringe housing 11, having a plunger end and a needle end, and wherein the plunger end accommodates an elongated tube-like plunger 12, which may be formed of essentially any cross-sectional shape, but is herein shown for convenience to be that of a cylindrical tube-like plunger, having a flanged end 13 and an open end covered with a diaphragm 14. The flange provides better control for retracting the plunger when filling the fluid holding chamber 10 and for providing a more accessible surface area for the thumb when using the syringe. The plunger is cylindrical in shape and has a diaphragm 14 sealing the open end of the plunger to effect, within the plunger 12, a hollow barrel area 15, in which the needle will be retracted and stored for disposition. The diaphragm 14 and plunger seal 16 may be molded as a single entity, or the diaphragm may be independent of the plunger seal 16 and held in place my some other method, such as a rubber or "Neoprene" seal which would hold the diaphragm taut across the open end of the plunger. The plunger seal 16 also functions to seal the space between the wall of the plunger housing 17 and the inside of wall 18 of the syringe housing 11, to assure against the leakage of fluid from the fluid holding chamber 10. The plunger 12 also has a small lip 19 extending outward from the outside surface of the plunger housing 17, which engages a plunger lock 20, extending inwardly from the inside wall 18 of the syringe housing 11. The lip 19 and the plunger lock 20 are so located on the outside surface of the plunger housing 17 and the inside of the wall of the syringe housing 11, respectively, that when the plunger reaches the bottom of its travel in the fluid holding chamber 10, the lip 19 and lock 20 become engaged and secure the plunger inside the syringe housing. This plunger locking mechanism serves to provide a means for safely encapsulating and storing the spent needle, until such time as it can be effectively disposed of.

Figure 4:
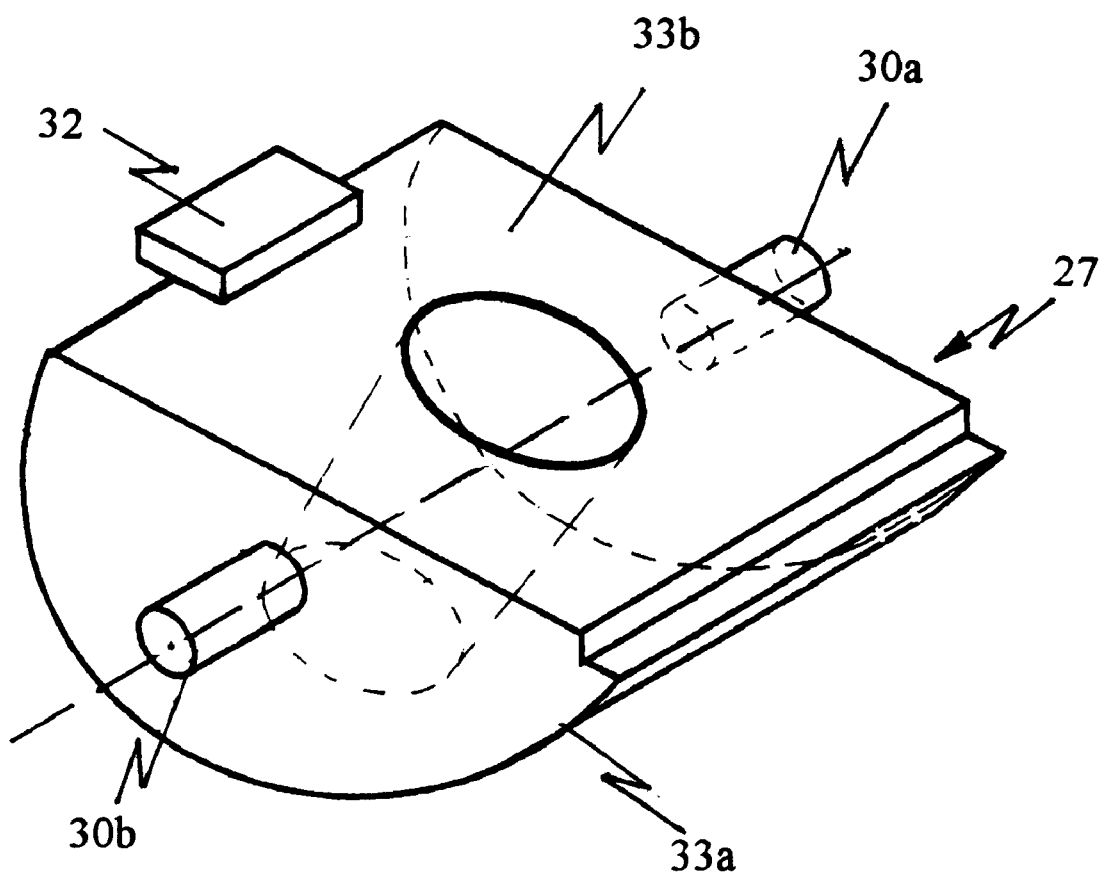
FIG. 4 is an isometric view of the rotating lock mechanism.
Figure 5:
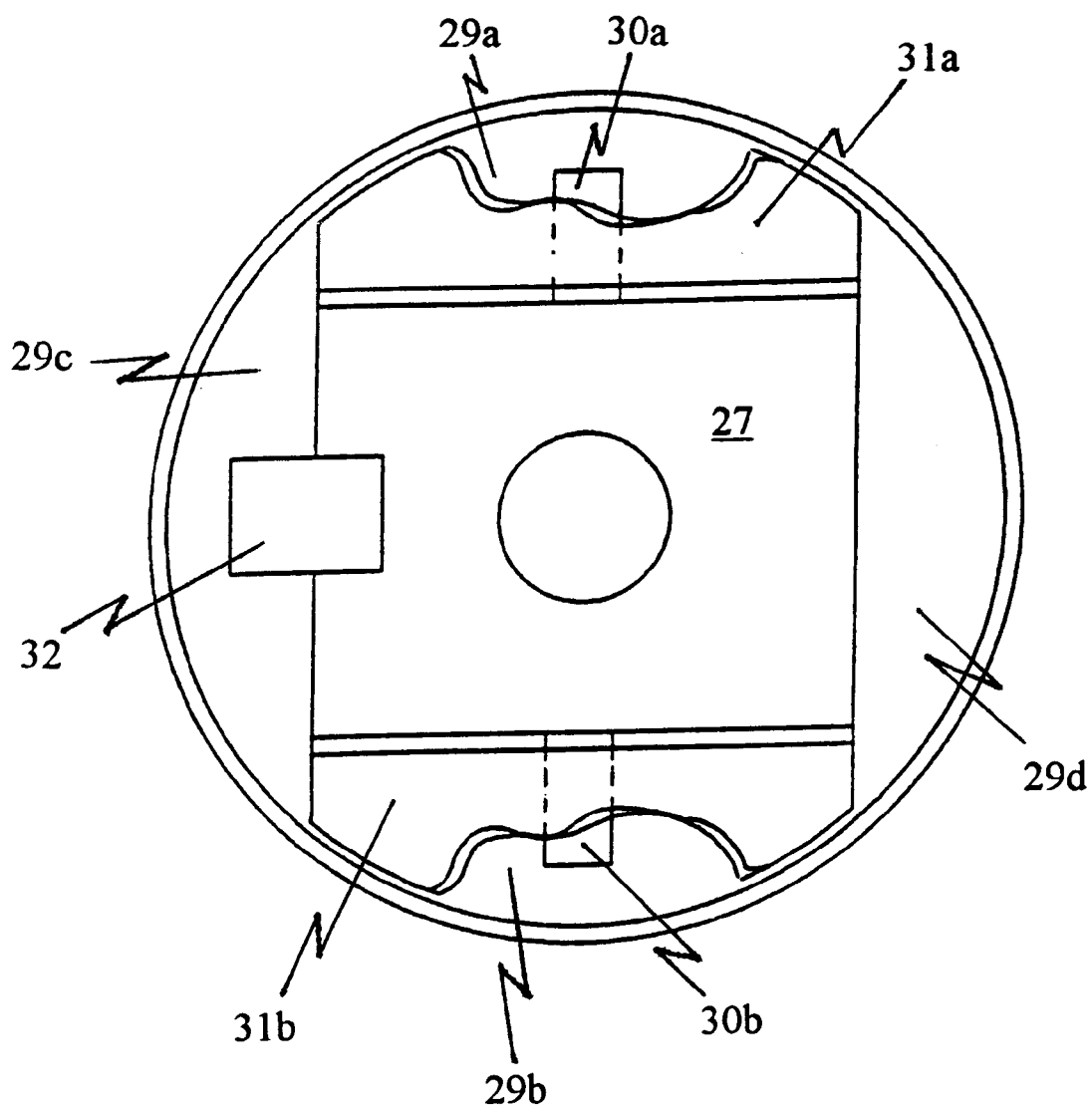
FIG. 5 is cross-sectional view of the syringe housing, showing how the rotating lock mechanism is seated, supported and locked into position.

Looking more specifically at the needle assembly, the retraction mechanism and the mechanism for holding the needle assembly at rest, our attention is drawn to FIG. 1, where the needle assembly is in a state of equilibrium. FIG. 3 more clearly shows the elements of the needle assembly to essentially be that of a needle 21, a needle sleeve 22, and a needle hub 23a. The needle hub 23a, is attached to one end of a needle 21 which extends through an opening in the needle end of syringe housing 11. The needle-hub 23 functions to seal the opening in the needle hub seal 23b in the neeedle end of the syringe housing 11, and provides a means against which one end of a compressed spring 24 is seated to place the needle under compression and to force the needle assembly into the interior of the syringe upon retraction of the needle. The needle passes through the spring 24 and through a syringe seal 8, upon which the other end of the spring 24 is seated. The needle 21 has a sleeve 22 surrounding a portion of the shaft of the needle which passes through the syringe seal 8 which provides a seal against the external leakage of fluids from the fluid holding chamber 10. The syringe seal 8 is seated in a needle assembly housing tip 25, which is coupled to the needle end of the syringe housing 11 to become an integral part thereof. The tip 25 may be attached to the syringe housing 11 by any of several techniques, such as by the use of mating threads (not shown) on the housing tip 25 and the syringe housing 11, by gluing, by using snap-on connectors or by heat spot welding. The housing tip 25 retains the syringe seal 8, the spring 24 and the needle 21. The housing tip 25 has a hole through the center of the tip such that the needle 21 will be properly aligned with the hole in the needle end of the syringe housing 11, the spring 24, and the syringe seal 8. The housing tip 25 also has a very small chamber 26 near the end of the housing tip 25 for collecting any body fluids remaining on the needle as it is retracted from the body of a patient. As the needle 21 is retracted back into the barrel of the syringe plunger 12, the syringe seal 8 wipes the needle 21 clean, and any fluids swiped from the needle is collected within the chamber 26, to assure that no fluids escape from the needle to contaminate the environment or infect a care-giver worker. The needle-hub 23a is held under compression force of the compressed spring 24 exerted on one side of the needle-hub 23, while a rotatable release member 27 sits atop the head of the needle-hub 23 and holds the needle assembly in a state of equilibrium. The second end of the syringe housing 11 contains a recess 28, having the same shape as the rotatable release member 27, to provide a seat for accepting the rotatable release member 27, which is a quasi-cylindrical member, as shown in FIG. 4, having a flat side 33b and an arcuate shaped side 33a, form fitted into the recess 28, as seen in FIG. 3. The needle end of the syringe housing, shown in FIG. 5, also contains support ledges 29a and 29b, on each side of the recess 28, to support the axles 30a and 30b of the rotating member 27, and ledges 29c and 29d at each end of the rotating lock mechanism, as shown in FIGS. 4 and 5. This entire rotatable release member support mechanism may be molded into the second end of the syringe housing or it may be fabricated as a separate unit and inserted into the housing of the syringe during the assembly of the automatically retractable hypodermic needle syringe.

Looking now at FIG. 4, one sees a more detailed view of the quasi-cylindrical rotatable member 27, which is in contact with and constrains the one end of the needle-hub 23a to maintain the needle assembly under compression. The rotating lock is caused to rotate by pressure being applied to plunger 12, whereby the plunger housing 17 of the diaphram covered end of the plunger 12 contacts the extension tab 32, of the rotating member 27, and as the plunger is mashed and further pressure is applied to the extension tab 32, the rotatable member 27 rotates in its seat and the filler sleeve insert 34 becomes aligned with the end of the needle-hub 23, thereby allowing the compressed needle assembly to force the filler sleeve insert 34 out of its seat in the hole of the rotatable member 27, and for the edge of the filler sleeve to puncture the diaphram 14 and be retracted through the hole in the rotatable member 27, and forced into the barrel of plunger 17, as shown in FIG. 2. The rotatable member 27 is supported within the recess 28 of the needle end of the syringe housing 11, by axles 30a and 30b supported by support shoulders 29a and 29b, and is held in place by ledge caps 31a and 31b, which may be secured to the axle supports 29a and 29b, by any of several well known techniques, such as by gluing or heat fusing. The rotatable member 27, is provided with a cylindrical hole in the center of the flat surface 27a, as shown in FIGS. 4 and 5. FIG. 4 shows an extension lip 32 firmly attached to one edge of the flat surface 27a, to stop the rotation of the rotatable member 27, when the rotatable member 27 rotates to the point where the extension 32 contacts the ledge 29c at the edge of the recess 28. At this point the hole in the rotatable member 27 is properly aligned with the needle assembly, whereby the spring forces the needle assembly into the plunger 12. It is necessary to provide a hole in the rotatable member 27 to allow the injection fluid to be exhausted form the fluid holding chamber 10, as a solid rotating lock would block the flow of any medicine from reaching the needle for injection into the patient. In order for the needle assembly to be retracted into the syringe plunger, the hole must be large enough to allow the needle assembly to pass therethrough and in order to prevent the needle assembly from binding on the lip of the hole, an insert must be provided which will allow any fluids in the fluid holding chamber 10 to be evacuated, while maintaining the needle assembly under compression. An insert in the form of a filler sleeve 34, being cylindrical on the outside and conical on the inside, is loosely but resistively seated into the hole in the rotatable member 27. The filler sleeve may be designed with a slightly jagged or pointed edge to aid in rupturing the diaphragm 14, of the plunger 12, during the retraction process. It became essential to provide a conical inner surface for the filler sleeve 34, as the assembly of the rotatable member 27 has to be initially tilted at a slight angle in order to maintain surface contact between the arcuate surface 33a and the top surface of the needle hub 23, to maintain the needle assembly in a state of equilibrium. Without the conical shaped passageway in the insert 24, tilting of the rotatable member 27 would either block the free flow of fluid through the hole in the insert 24, from the fluid holding chamber 10, or perhaps block the hole entirely and cut off the flow of the fluid. At least some portion of the arcuate surface 33a, of the rotatable member 27, must be in contact with the needle hub to provide a counterbalance on the needle hub for the force being applied to the needle by the compressed spring 24.

Looking now at FIG. 5, we see a cross sectional view of the needle end of the syringe housing 11, cut just above the rotatable member 27. The rotatable member 27 is shown seated in the recess 28 of the needle end of the syringe housing 11, with the flat side 33b, of the rotating member 27 facing upward. The axles 30a and 30b are seated in indentations in shoulder supports 29a and 29b and secured in place with axle hold downs 31a and 31b.

While this invention has been described in terms of a preferred embodiment consisting of a hypodermic needle which is automatically retracted into the barrel of the plunger when the fluids being injected have been evacuated from the syringe and the plunger reaches the end of its travel, those skilled in the art will recognize that the invention can be practiced with modification within the spirit and scope of the appended claims.

Having thus described my invention, what I claim as new and desire to secure by Letters Patent is as follows:

1. A hypodermic syringe comprising:

a syringe housing having plunger and needle ends with a cavity therebetween for storing fluids to be administered to a patient, with said plunger end accommodating a syringe plunger and said needle end accommodating an automatically retractable needle assembly and a needle release assembly;

a syringe plunger mated to the inside surface of the syringe housing with a pliable seal between the inside surface of the syringe housing and the outside surface of the plunger, said plunger having a housing with a closed end and an open end, wherein the closed end provides an end surface upon which pressure may be applied to the plunger to effect the movement of the plunger down the length of the syringe housing and into the lower portion thereof, with the open end being fitted with a thin membrane covering and sealing the end thereof, such that a vacuum is formed as the plunger is drawn toward the plunger end of the syringe housing, whereby a fluid may be drawn into the fluid holding chamber of the syringe and stored for use;

a needle assembly housing tip for housing an automatically retractable needle assembly, wherein said housing tip is an elongated extension to the syringe housing and contains a spring under compression to maintain a force on the needle for effecting the ejection of the needle into the barrel of the plunger upon release of the needle assembly;

means for coupling said needle assembly housing tip to the needle end of the syringe housing;

an automatically retractable needle assembly, including a hypodermic needle having a pointed end extending through said coupling means, with the other end having a needle hub attached thereto, wherein the compressed spring exerts a force on the needle hub in a direction to force the needle into the barrel of the plunger, upon activation of the retracting mechanism;

a rotatable release assembly, sitting atop the needle hub, holds the needle in a state of equilibrium until released, and includes a quasi-cylindrical rotatable member having an arcuate side and a substantially flat side, with said arcuate side seated within a conforming recess in the needle end of the syringe housing, said rotatable member having axle extensions extending longitudinally from the ends of the rotatable member and resting on shoulders within the syringe housing for supporting the rotatable member, said rotatable member further having a cylindrical passageway in the approximate center of the substantially flat side of the rotatable member for allowing the passage of the needle assembly therethrough during the automatic retraction of the needle, said passageway being fitted with an insert having a hole through the center thereof for allowing the free flow of injection fluids from the fluid holding chamber of the syringe housing to the hypodermic needle for use on a patient, said insert being loosely but frictionally fitted into the passageway, such that it can be easily dislodged by the needle hub upon activation of the automatically retractable needle, said rotatable member being rotated a few degrees from an imaginary cross-section of the syringe housing during the initial assembly, such that a solid portion of the arcuate side of the rotatable member remains in contact with the top of the needle hub to maintain the needle assembly in a state of equilibrium until such time as the needle assembly is released for storage, whereby, upon administering an injection to a patient, and as the plunger reaches the needle end of the syringe housing, the plunger makes contact with the edge of the rotatable member of the rotatable release assembly and gradually rotates the rotatable member until the opening in the center of the rotatable member becomes aligned with the needle hub of the needle assembly and simultaneously therewith, the compressed spring automatically forces the needle hub against the insert in the rotatable member, forcing the insert out of its resting place, extracting the needle from the patient, and thrusting the needle and its assembly through the opening in the rotatable member into the barrel of the plunger for storage.

2. The hypodermic syringe of claim 1, wherein the rotatable member of the rotatable release assembly is fitted with an extension lip firmly attached to the edge of the elevated flat side of the rotatable member, such that contact between the rotatable member and the end of the housing of the plunger may be firmly effected.

3. The hypodermic syringe of claim 1, wherein the insert in the passageway of the rotatable member of the rotatable needle release assembly is cylindrically shaped on the outside with a conically shaped opening in the center thereof, with the small end of the conical opening beginning on the flat side of the rotatable member and extending therethrough to the larger opening on the arcuate side of the rotatable member.

4. The hypodermic syringe of claim 2, wherein the insert in the passageway of the rotatable member of the rotatable needle release assembly is cylindrically shaped on the outside with a conically shaped opening in the center thereof, with the small end of the conical opening beginning on the flat side of the rotatable member and extending therethrough to the larger opening on the arcuate side of the rotatable member.

5. The hypodermic syringe of claim 1, wherein the needle assembly housing tip, coupled to the needle end of the syringe housing, also contains a seal, through which the needle passes, which functions to seal the fluid within the chamber of the syringe housing and to prevent any leakage of fluid therefrom.

6. The hypodermic syringe of claim 2, wherein the needle assembly housing tip, coupled to the needle end of the syringe housing, also contains a seal, through which the needle passes, which functions to seal the fluid within the chamber of the syringe housing and to prevent any leakage of fluid therefrom.

7. The hypodermic syringe of claim 3, wherein the needle assembly housing tip, coupled to the needle end of the syringe housing, also contains a seal, through which the needle passes, which functions to seal the fluid within the chamber of the syringe housing and to prevent any leakage of fluid therefrom.

8. The hypodermic syringe of claim 4, wherein the needle assembly housing tip, coupled to the needle end of the syringe housing, also contains a seal, through which the needle passes, which functions to seal the fluid within the chamber of the syringe housing and to prevent any leakage of fluid therefrom.

9. The hypodermic syringe of claim 1, wherein the speed of retraction of the needle from the body of a patient is controlled by providing a needle sleeve approximately midway between the tip of the needle and the needle hub, and varying the thickness of the sleeve, or alternatively, the size of the hole in the seal through which the needle passes to control the friction between the needle sleeve and the sides of the hole and thus, control the speed of retraction of the needle.

10. The hypodermic syringe of claim 1, wherein a fluid catching chamber is molded into the very tip of the needle assembly housing tip, whereby any body fluids from the patient adhering to the of the needle is wiped from the surface of the needle by the seal and collected in the fluid catching chamber.

* * * * *